United States Patent [19]

Cyprien et al.

[11] Patent Number: 5,114,707
[45] Date of Patent: * May 19, 1992

[54] POLYCONDENSATION SILICONE ELASTOMER DOSAGE FORMS FOR THE CONTROLLED RELEASE OF IODINE VALUES

[75] Inventors: Guy Cyprien, L'Hay les Roses; Alain Fisch, Paris; Johnny Haggiage, Lyons; Hugues Porte, Caluire; Thierry Prazuck, Paris; Ghislaine Torres, Lyons, all of France

[73] Assignee: Rhone-Poulenc Chimie, Courbevoie, France

[ * ] Notice: The portion of the term of this patent subsequent to Dec. 12, 2006 has been disclaimed.

[21] Appl. No.: 625,708

[22] Filed: Dec. 11, 1990

Related U.S. Application Data

[63] Continuation of Ser. No. 161,445, Feb. 26, 1988, abandoned.

[30] Foreign Application Priority Data

Feb. 26, 1987 [FR] France .................. 87 02883

[51] Int. Cl.$^5$ ................. A61K 31/73; A01N 59/12
[52] U.S. Cl. ................ 424/667; 424/672; 514/743
[58] Field of Search .............. 424/78, 150, 672; 528/15, 31, 32; 524/861, 862

[56] References Cited

U.S. PATENT DOCUMENTS

| | | | |
|---|---|---|---|
| 2,798,023 | 7/1957 | Berge | 424/150 |
| 2,918,400 | 12/1959 | Loonanm | 424/78 |
| 3,330,885 | 7/1967 | Dalton | 424/80 |
| 4,012,497 | 3/1977 | Schopflin | 424/22 |
| 4,053,580 | 10/1977 | Chien et al. | 424/425 |
| 4,107,346 | 8/1978 | Krantz | 426/648 |
| 4,275,194 | 6/1981 | Kato et al. | 536/20 |
| 4,384,960 | 5/1983 | Polley | 424/150 |
| 4,420,590 | 12/1983 | Gartner | 525/357 |
| 4,500,337 | 2/1985 | Young et al. | 71/67 |
| 4,640,956 | 2/1987 | Toub et al. | 524/779 |
| 4,886,661 | 12/1989 | Guy et al. | 424/78 |

FOREIGN PATENT DOCUMENTS 1467861 1/1969 Fed. Rep. of Germany .
1412970 11/1975 United Kingdom .

Primary Examiner—Lester L. Lee
Attorney, Agent, or Firm—Burns, Doane, Swecker & Mathis

[57] ABSTRACT

Polycondensation silicone elastomer dosage forms adapted for the continuous and controlled release of iodine values, notably to domestic water supplies for the treatment of the various disease states attributed to iodine deficiency, are shaped from (A) at least one diorganopolysiloxane oil bearing at least two condensable or hydrolyzable groups, or a single hydroxyl group, at each end of the polymer chain; (B) a therapeutically effective amount of at least one water soluble, nontoxic, organic and/or inorganic iodine compound which is in solid or liquid state at ambient temperature and which does not inhibit curing of the composition into an elastomer; (C) a catalytically effective amount of a polycondensation catalyst; and optionally, (D) a silane containing at least three condensable or hydrolyzable groups.

17 Claims, No Drawings

POLYCONDENSATION SILICONE ELASTOMER DOSAGE FORMS FOR THE CONTROLLED RELEASE OF IODINE VALUES

This application is a continuation of application Ser. No. 07/161,445 filed Feb 26, 1988, and now abandoned.

CROSS-REFERENCE TO COMPANION APPLICATIONS

Our copending application Ser. Nos. 161,173, 161,443, and 161,133, all filed concurrently herewith and all assigned to the assignee hereof.

BACKGROUND OF THE INVENTION

1. Field of the Invention

The present invention relates to compositions based on polycondensation-curable diorganopolysiloxane oils and containing iodine, to dosage forms shaped therefrom and adapted for the controlled release of iodine values, and to a process for treating domestic water supplies and beverages utilizing such compositions/dosage forms.

2. Description of the Prior Art

The number of subjects exhibiting a deficiency or an inadequacy of iodine is currently estimated at several hundred million worldwide. The geographical regions affected to the greatest degree are Latin America, particularly along the Andean Cordillera, and virtually all the non-coastal regions of Africa and of Asia (Pakistan, India, Nepal, China, Laos, etc.).

The principal pathological consequences of iodine deficiency are well known. These are essentially, on the one hand, goiter and its complications, among which may be included swallowing disorders, respiratory disorders, cancer, peripheral circulation and, on the other hand, hypothyroidism and its complications, among which may be mentioned: cretinism, cerebral disorders, premature births, miscarriages and congenital abnormalities.

While iodine deficiency has disappeared from industrialized countries because, for example, the salts used for cooking are iodized, this is not the case in the developing countries, where the two main campaigns undertaken to date have proven ineffective.

These campaigns have for their focus, on the one hand:

(i) the iodination of cooking salt: this is not effective in the majority of the developing countries because very frequently the consumption of salt is minimal, the systems for the distribution of salt via the economic and commercial networks are virtually nonexistent and, finally, in a tropical region, iodine which is added to salt escapes rapidly if it is not perfectly packaged;

and, one the other hand:

(ii) the intramuscular injection of iodinated oil: this injection has the advantage of exhibiting a delayed action, but it is not devoid of disadvantages, particularly the risks of infection, the risks of iodine allergy, and the risks of hyperthyropidism or of hypothyroidism, which are caused by the injection of a necessarily supraphysiological dosage.

Furthermore, Belgian Patent BE-A-889,680 describes the introduction of oligoelements, including iodine, into the drinking water of ruminants, in the form of a dispersion in a binder such as, for example, plaster of Paris. A diorganopolysiloxane may be added with a view to slowing the diffusion of the oligoelement. In addition, the use of iodine and of iodine compounds for disinfecting or for purifying water is well known. Compare, for example, U.S. Pat. Nos. 2,347,567, 2,743,208 and 3,408,295.

There also exist very many patents describing the use of polymeric systems, especially silicone, for the controlled release of an active ingredient, for example by means of a transdermal system (U.S. Pat. No. 4,053,580), or by oral ingestion, especially for ruminants (French Patent FR-A-2,560,768).

Lastly, U.S. Pat. No. 4,384,960 describes placing iodine $I_2$ tablets in a plastic bottle, into which water enters through a porous polymer membrane. The water dissolves the iodine. The purpose of the membrane is merely to prevent the iodine tablets from leaving the bottle.

It is simply suggested, furthermore, that it is possible to introduce iodine $I_2$ into the bottle in a liquid dispersion of silicone or of a dimethylsiloxane elastomer, and then to cure them. This suggested solution is not technically feasible because, firstly, $I_2$ is a well-known inhibitor of the catalysts for curing silicone elastomers capable of being vulcanized at ambient temperature (see, in particular, the publication by W. D. Morain et al., *Plastic and Reconstructive Surgery*, 59, 2, 215–222 (1977)) and, secondly, because of its high volatility, $I_2$ sublimes during the crosslinking of silicone elastomers when heated.

However, in this system, not only is there no control over the release of iodine, but also the iodination of water takes place by noncontinuous or continuous addition of a few drops of highly iodized (to saturation) water contained in the bottle, to any receptacle containing untreated water. It is clear that the solution proposed by U.S. Pat. No. 4,384,960 is imperfect, especially because of the fact that it involves an individual method which, like the intramuscular injection of iodine, requires mass education and mobilization of entire populations.

SUMMARY OF THE INVENTION

Accordingly, a major object of the present invention is the provision of a polycondensation silicone elastomer composition containing iodine and suitable for use for the continuous treatment of water for domestic purposes, particularly in water supply and treatment systems in wells and boreholes. The subject composition makes it possible to distribute (release) a controlled and measured amount of iodine with a view to ensuring the collective treatment of the various manifestations due to an iodine deficiency, as well as a prophylaxis of these various manifestations.

Another object of the invention is to provide a polycondensation silicone elastomer composition containing iodine which, when suitably immersed in water sources to be treated, especially wells and boreholes, continually distributes (releases), preferably for at least one year, an appropriate amount of iodine in a therapeutically active and effective form and dosage in order to treat the various diseases caused by iodine deficiency.

Yet another object of the invention is to provide a polycondensation silicone elastomer composition containing iodine which, when suitably immersed in water sources to be treated, has no undesirable secondary or side effects which are detrimental to the water to be treated from a chemical and biological standpoint.

Still another object is to provide a polycondensation silicone elastomer composition containing iodine, in a form which is adapted to the environment in which the water to be treated is found, this form being particularly adapted to wells and/or bore-holes and offering a system for introduction into the wells and/or boreholes permitting it to be easily replaced.

Another object of the invention is to provide a silicone elastomer polycondensation composition containing iodine which is contributed by an iodine compound which does not inhibit the cure (crosslinking) of the polycondensation silicone composition into an elastomer.

Briefly, the present invention features polycondensation-curable silicone composition, comprising:

(A) at least one diorganopolysiloxane oil bearing at least two condensable or hydrolyzable groups, or a single hydroxyl group, at each end of its polymer chain;

(B) at least one organic and/or inorganic iodine compound in solid or liquid form at ambient temperature, soluble in water, nontoxic and which does not inhibit the cure of the composition into an elastomer;

(C) a catalytically effective amount of a polycondensation catalyst; and, optionally, (D) a silane containing at least three condensable or hydrolyzable groups, and necessarily so when (A) is an oil with hydroxyl end groups.

DETAILED DESCRIPTION OF THE PREFERRED EMBODIMENTS OF THE INVENTION

More particularly according to the present invention, exemplary of the inorganic iodine compounds, representative are, whether singly or in admixture:

iodides or iodates of the general formulae:

$$(M^{a+})(I^-)_a$$

and $$(M^{a+})(IO_3^-)_a$$

in which a is an integer greater than or equal to 1 and M is a cation selected from among an alkali metal such as sodium and potassium, an alkaline earth metal such as magnesium and calcium, a transition metal such as iron and manganese, a quaternary ammonium $(NY_4)^+$, in which the radicals Y, which may be identical or different, are each a linear or branched chain $C_1$–$C_{20}$ alkyl radical or a hydrogen atom, such as the ammonium ion $NH_4^+$.

The cations $M^{a+}$ and $NY_4^+$ are selected such that the corresponding iodide or iodate is a solid or a liquid at ambient temperature, is soluble in water and is nontoxic.

The iodides and iodates which may be employed are particularly those of the formulae:

$NaI, NaIO_3,$ $KI, KIO_3,$ $MgI_2, M_gI_2.8H_2O,$ $Mg(IO_3)_2.4H_2O,$ $NH_4I,$ $FeI_2.4H_2O$ $MnI_2.$

These salts may contain water of hydration or water of formation.

As a compound of iodine which is both organic and inorganic, representative is, for example, calcium iodobehenate of the formula:

$$(C_{21}H_{42}ICO_2)Ca$$

Iodinated polyvinylpyrrolidone is exemplary of an organic iodine compound.

For reasons of ease of use, solid iodine compounds are preferred, and NaI and $KIO_3$ are the most preferred among these.

All the iodine compounds such as defined above release iodine in a nontoxic and therapeutically effective form when they are dissolved in the water to be treated.

By "nontoxic iodine compound" according to the invention is intended a compound which, in solution, is not toxic in the dosages contemplated hereby.

By "water-soluble iodine compound" is intended a compound having a solubility of at least 100 μg/l at ambient temperature.

From 5 to 130 parts and preferably from 10 to 100 parts of iodine compound (B) are generally employed per 100 parts of the oil (A).

Furthermore, the iodine compounds must not inhibit the curing of the silicone composition into an elastomer. Molecular iodine $I_2$ is therefore excluded from the iodine compounds capable of being employed according to the present invention.

In the developing countries in particular, water for domestic use (drinking, washing, irrigation, and the like) is essentially provided by structures of two types, wells and boreholes.

For obvious reasons of cost, efficiency and salubriousness, the creation of a new water source is frequently produced by drilling.

A borehole is a column of air drilled through compact rock formations having a depth which is generally between 20 and 100 meters and a diameter of at least approximately 10 cm. Water filters into this column through cracks or various interstices. The water reserve which is immediately available thus consists of a column of 10 to 70 meters, generally from 30 to 50 meters, in height, which is withdrawn with the aid of an immersed-body pump.

This water is renewed chiefly as a function of the use of the borehole, which depends on the season. In fact, in the rainy season the borehole is traditionally used less. On the other hand, in the dry season the borehole is used for approximately 10–12 hours daily, which is a quantity of between 5 and 10 m³ per day for approximately six months.

As a general rule, a well may be run dry twice daily in the dry season, which corresponds to a maximum usage of 5 to 10 m³, based on these average statistical data.

Numerous studies show that in the regions of the world which are highly endemic in goiter, the preexisting proportion of iodine equivalent in the water in boreholes or in wells is less than 2 micrograms per liter (2 μg/l). It is currently estimated that a daily input of approximately 100 μg of iodine equivalent per day per person would be sufficient to prevent the development of endemic goiter and doubtless approximately 150 μg in the presence of regular consumption of goiterogenic substances. Conversely, acute iodine intoxication may be responsible for neurological irritation, for hyperthyroidism or for hypothyroidism.

It is assumed in the medical arts that the ingestion of a dose of 3 grams of iodine equivalent by an adult subject, as a single dose, does not produce any secondary effect.

Consequently the objective is to make it possible to provide an individual with 20 to 200 µg, preferably approximately 100 µg, of iodine equivalent daily.

Thus, with the knowledge that, on average, an adult individual ingests 2 liters of water daily and on the basis of the above data (a borehole with an output of 600 l/hr), it appears desirable that one liter of treated water should contain approximately 50 µg/l of iodine, which corresponds to 50 µg of iodine equivalent per liter per person, which requires the silicone composition to release 720 mg/d of iodine equivalent, i.e., 270 g of iodine equivalent to be released over one year.

Unless indicated otherwise, the parts and percentages given herein are by weight.

Surprisingly and unexpectedly, it has now in fact been found, according to the present invention, that it is possible to incorporate into a silicone resin large quantities of iodine compound in a solid or liquid form such as defined above, namely from 5 to 150 parts, preferably from 20 to 100 parts per 100 parts of a diorganopolysiloxane resin filled with a reinforcing filler, and thus to obtain a product which, even in the absence of a crosslinking and/or antistructuring agent has sufficient mechanical characteristics for the intended application and which makes it possible to ensure a continuous and controlled release of iodine, preferably for at least one year, when immersed in water.

The controlled iodine release system forms part of the matrix systems in which the diffusion of the active ingredient is normally determined by Fick's Law, that is to say, by diffusion kinetics on the order of ½ for only 60% by weight of the active principal. Beyond 60% the matrix is exhausted and the diffusion fluxes are greatly reduced. Surprisingly and unexpectedly, it has been found that the silicone matrix system according to the invention continuously releases iodine according to zero-order kinetics and does so until 80% by weight and more of the iodine compound has been released.

The considerable advantage contributed by the silicone matrix is, therefore, that it is very easy to extrapolate the continuous diffusion of the active ingredient after a measurement of the quantity released after at leas one month, because it is known that the diffusion kinetics are of zero order and that at least 80% of the iodine compound will be released according to these kinetics.

In order to gain complete control of the release of the active ingredient it is advantageous to shape the silicone matrix in the form of elementary modules (elements) of various shapes such as cubes, right parallelepipeds, cylinders and spheres, whose fundamental parameters are the following:

(a) the nature of the iodine compound;
(b) the mean diameter (particle size) g of the particles of the iodine compound in the preferred case where the latter is a solid;
(c) the concentration of the iodine compound within the matrix;
(d) the surface/volume ratio R of the module.

The nature of the iodine compound and its particle size define the rate of diffusion of the active ingredient through the matrix.

The lower the value of g, the slower v is and vice versa.

The higher the value of t, the greater the flux of active ingredient and vice versa.

The higher the value of R, the greater the high flux of active ingredient and vice versa.

One skilled in this art, using routine experiments, is capable of rapidly and without difficulty obtaining the required result by extrapolating the theoretical elution time which will correspond to the actual time of diffusion of the active ingredient.

In the case of NaI and KIO$_3$, which are the preferred iodine compounds, g, t and R may advantageously be within the following ranges:

(i) g of from 1 to 300 µm;
(ii) t of from 10 to 100 parts by weight of iodine compound per 100 parts of (A); and
(iii) R of from 0.5 to 50 in the case of a cylindrical shape.

It is desirable, furthermore, that the iodine compound should be dispersed homogeneously throughout the matrix.

The diorganopolysiloxane oils (A) suitable for use in the compositions according to the invention are more advantageously those corresponding to the formula (1):

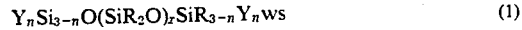

$$Y_nSi_{3-n}O(SiR_2O)_xSiR_{3-n}Y_nws \qquad (1)$$

in which:

R denotes identical or different monovalent hydrocarbon radicals, Y denotes identical or different hydrolyzable or condensable groups or hydroxy groups, n is 1,2 and 3, with n=1 when Y is a hydroxyl group and x is an integer greater than 1, preferably greater than 10.

The viscosity of the oils of formula (1) ranges from 50 to $10^6$ mPa.s at 25° C. As specific examples of the radicals R, representative are alkyl radicals containing from 1 to 8 carbon atoms such as methyl, ethyl, propyl, butyl, hexyl and octyl radicals, vinyl radicals, and phenyl radicals. As examples of substituted radicals R, representative are 3,3,3-trifluoropropyl, chlorophenyl and beta-cyanoethyl radicals.

In the oils of formula (1) which are generally employed industrially, at least 60%, on a numeral basis, of the radicals R are methyl radicals; the other radicals are generally phenyl and/or vinyl radicals.

As examples of hydrolyzable groups Y, representative are amino, acylamino, aminoxy, ketimonxy, iminoxy, enoxy, alkoxy, alkoxylalkyleneoxy, acyloxy and phosphato groups.

As examples of the amino Y groups, representative are n-butylamino, sec-butylamino and cyclohexylamino groups. An exemplary N-substituted acylamino group is the benzoylamino group. Exemplary aminoxy groups are the dimethylaminoxy, diethylaminoxy, dioctylaminoxy and diphenylaminoxy groups. Exemplary iminoxy and ketiminoxy Y groups are those derived from acetophenone oxime, acetone oxime, benzophenone oxime, methyl ethyl ketoxime, diisopropyl ketoxime and chlorocyclohexanone oxime.

Exemplary of the alkoxy Y groups, representative are the groups containing from 1 to 8 carbon atoms such as methoxy, ethoxy, propoxy, isopropoxy, butoxy, hexyloxy and octyloxy groups. Exemplary of an alkoxyalkyleneoxy Y group is the methoxyethyleneoxy group.

As acyloxy Y groups, representative are groups containing from 1 to 8 carbon atoms such as formyloxy, acetoxy, propionyloxy and 2-ethylhexanoyloxy groups.

As phosphato Y groups, representative are those derived from dimethyl phosphate, diethyl phosphate and dibutyl phosphate.

As condensable Y groups, representative are hydrogen atoms and halogen atoms, preferably chlorine.

When the groups Y in the formula (1) above ar hydroxyl groups, n is then equal to 1, and in order to prepare polyorganosiloxane elastomers from polymers of formula (1) above, it is necessary to employ, in addition to condensation catalysts, crosslinking agents (D), indicated above, which are silanes of the general formula:

$$R_{4-a}SiY'_a \quad (2)$$

in which
R is as defined above in formula (1) and Y' denotes identical or different hydrolyzable or condensable groups, and
a is equal to 3 and 4.

The examples given in the case of the groups Y are also applicable to the groups Y'.

It is desirable to employ silanes of formula (2) even in the case where Y in the oil (A) is not a hydroxyl group.

In this case, it is desirable to employ groups Y in the oil (A) which are identical with Y' in the silane (D).

The alpha,omega-dihydroxylated diorganopolysiloxanes of formula (1) are typically oils whose viscosity ranges from 500 mPa.s at 25° C. to 500,000 mPa.s at 25° C., preferably 800 mPa.s to 400,000 at 25° C.; they are linear polymers consisting essentially of diorganosiloxy units of formula ($R_2SiO$). However, the presence of other units, generally present as impurities, such as $RSiO_{3/2}$, $RSiO_{\frac{1}{2}}$ and $SiO_{4/2}$ is also within the ambit of the invention, in a proportion not exceeding 1% based on the number of diorganosiloxy units.

The organic radicals bonded to the silicon atoms of the base oils and denoted by the symbol R may be selected from alkyl radicals containing from 1 to 3 carbon atoms such as methyl, ethyl and n-propyl radicals, the vinyl radical, the phenyl radical, the 3,3,3-trifluoropropyl radical and the beta-cyanoethyl radical.

At least 60% of the total of the radicals R are methyl radicals; not more than 1% are vinyl radicals.

By way of illustration of the units denoted by the formula $R_2SiO$, representative are those of the formulae: $(CH_3)_2SiO$, $CH_3(CH_2=CH)SiO$, $CH_3(C_6H_5)SiO$, $CF_3CH_2CH_2(CH_3)SiO$, $NC-CH_2CH_2(CH_3)SiO$, $NC-CH_2(C_6H_5)SiO$.

These base oils are, for the most part, commercially available from the silicone manufacturers. Furthermore, processes for the preparation thereof are well known to the art and are described, for example, in French Pat. Nos. 1,134,005, 1,198,749 and 1,226,745.

As specific examples of monomeric silanes (D) of formula (2), more particularly representative are polyacyloxysilanes, polyalkoxysilanes, polyketiminoxysilanes and polyiminoxy-silanes and, in particular, the following silanes: $CH_3Si(OCOCH_3)_3$, $C_2H_5Si(OCOCH_3)_3$, $CH_2=CHSi(OCOCH_3)_3$, $C_6H_5Si(OCOCH_3)_3$, $CF_3CH_2CH_2Si(OCOCH_3)_3$, $NC-CH_2CH_2Si(OCOCH_3)_3$, $CH_2ClSi(OCOCH_2CH_3)_3$, $CH_3Si(ON=C(CH_3)C_2H_5)_2OCH_2CH_2OCH_3$, $CH_3Si(ON=CH-CH_3)_2OCH_2CH_2OCH_3$.

The above silanes (D) associated with alpha,omega-dihydroxylated polydiorganosiloxanes of formula (1) may be employed in single-component compositions which are stable in the absence of air.

As examples of a monomeric silane of formula (2) which, when associated with alpha,omega-dihydroxylated polydiorganosiloxanes of formula (1), may be advantageously employed in two-component compositions, polyalkoxysilanes are representative, and particularly those of formulae: $Si(OC_2H_5)_4$, $Si(O-n-C_3H_7)_4$, $Si(O-isoC_3h_7)_4$, $Si(OC_2H_4OCH_3)_4$, $CH_3Si(OCH_3)_3$, $CH_2=CHSi(OCH_3)_3$, $CH_3Si(OC_2H_4OCH_3)_3$, $ClCH_2Si(OC_2H_5)_3$, $CH_2=CHSi(OC_2H_4OCH_3)_3$.

All or a part of the monomeric silanes described above may be replaced by polyalkoxypolysiloxanes n which each molecule contains at least two, preferably three Y' atoms and the remaining valences of silicon are satisfied by siloxane bonds SiO— and SiR. Ethyl polysilicate is an example of a polymeric crosslinking agent.

From 0.1 to 20 parts by weight of crosslinking agent of formula (2) are generally employed per 100 parts by weight of polymer of formula (1).

The polyorganosiloxane compositions capable of being cured to an elastomer of the type described above contain from 0.001 to 10 parts by weight, preferably from 0.05 to 3 parts by weight of condensation catalyst (C) per 100 parts by weight of polysiloxane of formula (1).

The content of condensation catalyst in the single-component compositions is generally much lower than that employed in the two-component compositions and is generally from 0.001 to 0.05 part by weight per 100 parts by weight of polysiloxane of formula (2).

Whether they be employed for the preparation of single-component or two-component compositions, the crosslinking agents (D) of formula (2) are commercially available on the silicone market. Furthermore, their use in the compositions which cure from ambient temperature and higher is known (see particularly French Patents Nos. 1,126,411, 1,179,969, 1,189,216, 1,198,739, 1,248,826, 1,314,649, 1,423,477, 1,432,799 and 2,067,636.

The compositions according to the invention may additionally contain reinforcing or semireinforcing or extending fillers (E) which are preferably siliceous fillers, pyrogenic silicas and precipitated silicas. They have a specific surface area, measured according to the BET method, of at least 50 $m^2/g$, preferably greater than 70 $m^2/g$, a mean primary particle size of less than 0.1 μm (micrometer) and an apparent density of less than 200 g/liter.

These silicas may be incorporated preferably as such or after they have been treated with the organosilicon compounds which are usually employed for this purpose. These compounds include methylpolysiloxanes such as hexamethyldisiloxane and octamethylcyclotetrasiloxane, methylpolysilazanes such as hexamethyldisilazane and hexamethylcyclotrisilazane, chlorosilanes such as dimethyldichlorosilane, trimethylchlorosilane, methylvinyldichlorosilane and dimethylvinylchlorosilane, and alkoxysilanes such as dimethyldimethoxysilane, dimethylvinylethoxysilane and trimethylmethoxysilane. In the course of this treatment, the silicas may increase in their initial weight up to a proportion of 20%, preferably approximately 18%

The semireinforcing or extending fillers have a particle diameter greater than 0.1 μm and are selected from among ground quartz, calcined clays and diatomaceous earths.

From 0 to 100 parts, preferably from 5 to 50 parts of filler (E) may generally be employed per 100 parts of oil (A).

The silicone composition bases defined generally above are well known to this art. They are described in detail in the literature, particularly in many patents and the majority are commercially available.

These compositions crosslink at ambient temperature in the presence of moisture contributed by atmospheric moisture and/or present in the composition. They may be divided into two large classes. The first class consists of single-component or single-pack compositions which are stable in storage in the absence of atmospheric moisture and which cure to an elastomer in the presence of atmospheric moisture. In this case the condensation catalyst (C) employed is a metal compound, generally a tin, titanium or zirconium compound.

According to the nature of the condensable or hydrolyzable groups, these single-component compositions are referred to as acidic, neutral or basic.

As acidic compositions, it is possible to employ, for example, the compositions described in U.S. Pat. Nos. 3,035,016, 3,077,465, 3,133,891, 3,409,573, 3,438,930, 3,647,917, and 3,886,118.

As the neutral compositions, it is possible to employ, for example, the compositions described in U.S. Pat. Nos. 3,065,194, 3,542,901, 3,689,454, 3,779,986, 4,417,042, British Patent No. 2,052,540, and European Application 69,256.

As the basic compositions, it is possible to employ, for example, the compositions described in U.S. Pat. Nos. 3,378,520, 3,364,160, 3,417,047, 3,464,951, 3,742,004, and 3,758,441.

In a preferred alternative embodiment, it is also possible to employ single-component flowing compositions such as those described in U.S. Pat. Nos. 3,922,246, 3,965,280, and 4,143,088.

The second class is the preferred class according to the present invention and consists of the two-component or two-pack compositions, generally containing an alpha,omega-dihydroxydiorganopolysiloxane oil (A), a silane (D) or a product originating from the partial hydrolysis of this silane, and a catalyst (C) which is a metal compound, preferably a tin compound and/or an amine.

Examples of such compositions are described in U.S. Pat. Nos. 3,678,002, 3,888,815, 3,933,729, 4,064,096, and British Patent No. 2,032,936.

Among such compositions, those more particularly preferred are the two-component compositions containing:

(A): 100 parts of an alpha,omega-dihydroxyorganopolysiloxane oil having a viscosity of 50 to 300,000 mPa.s in which the organic radicals are methyl, ethyl, vinyl, phenyl and 3,3,3-trifluoropropyl radicals, at least 60% of their number being methyl radicals, up to 20% of their number being phenyl radicals, and not more than 2% being vinyl radicals;
(B): 10 to 130 parts of an iodine compound;
(C): 0.01 to 1 part (calculated as the weight of tin metal) of a catalytic tin compound;
(D): 0.5 to 15 parts of a polyalkoxysilane or a polyalkoxysiloxane; and
(E): 0 to 100 parts, preferably 5 to 50 parts, of siliceous inorganic filler.

The tin catalysts (C) are well described in the literature referred to above. In particular, this may be a tin salt of a mono- or dicarboxylic acid. These tin carboxylates are particularly described in the text by Noll (*Chemistry and Technology of Silicones*, page 337, Academic Press, 1968, 2nd edition). Dibutyltin naphthenate, octanoate, oleate, butyrate and dilaurate, and dibutyltin diacetate are preferred.

The product of reaction of a tin salt, especially of a tin dicarboxylate, with ethyl polysilicate, as described in U.S. Pat. No. 3,186,963, may also be used as a catalytic tin compound. The product of reaction of a dialkyldialkoxysilane with a tin carboxylate, as described in U.S. Pat. No. 3,862,919, may also be employed.

The product of reaction of an alkyl silicate or of an alkyltrialkoxysilane with dibutyltin diacetate, as described in Belgium Patent 842,305 may also be employed.

Among the crosslinking agents (D), those more particularly preferred are the alkyltrialkoxysilanes, alkyl silicates and alkyl polysilicates in which the organic radicals are alkyl radicals containing from 1 to 4 carbon atoms.

The alkyl silicates may be methyl silicate, ethyl silicate, isopropyl silicate, n-propyl silicate and the polysilicates selected from among the products of partial hydrolysis of these silicates. These are polyers including a high proportion of units of the formulae $(R^4O)_3SiO_{0.5}$, $R^4OSiO_{1.5}$, $(R^4O)_2SiO$ and $SiO_2$; the symbol $R^4$ denoting the methyl, ethyl, isopropyl and n-propyl radicals. They are usually characterized on the basis of their silica content which is established by determining the product of complete hydrolysis of a sample.

The polysilicate employed may be, in particular a partially hydrolyzed ethyl silicate marketed under the trademark "Ethyl Silicate-40" by Union Carbide corporation, or a partially hydrolyzed propyl silicate.

The compositions according to the invention may be extruded or molded into a variety of shapes, for example in the shape of unit modules (elements) and may then be cured at ambient temperature to an elastomer in contact with atmospheric moisture or by the addition of water. A slight heating to a temperature of 20° to 150° C. may accelerate the cure.

The variously shaped elastomer modules (elements) may be maintained immersed in the water to be treated according to a quantity (a weight of elastomer) such that the elastomer ensures a continuous and controlled release of iodine, preferably for at least one year. At the end of this period, the modules (elements) are replaced.

Surprisingly, it has been found that these crosslinked silicone compositions have sufficient physical characteristics for the intended applications.

In order to further illustrate the present invention and the advantages thereof. The following specific examples are given, it being understood that same are intended only as illustrative and in nowise limitative.

EXAMPLE 1

A dough was prepared by kneading:
(i) 75 parts of alpha,omega-dihydroxymethylpolysiloxane oil having a viscosity( of 15,000 mPa.s at 25° C.;
(ii) 22.2 parts of celite (diatomaceous earth);
(iii) 2.3 parts of n-propyl silicate; and (iv) 0.5 part of a hydrated dough (mixture of dimethyl polysiloxane oil and pyrogenic silica) containing 5% of water.

The mixture was homogenized for 4 hours and was then filtered.

25 parts of NaI having a mean particle size of 5 μm were added to 100 parts of this dough.

A flowing product was obtained, which was catalyzed by the addition of 0.5 part of tin 2-ethylhexanoate.

The product was poured into molds made of steel covered with an antiadhesive agent (Melinex), of cylindrical shape (diameter equal to 10 mm).

After 1 hour at 100° C., a well-crosslinked product was obtained, which had sufficient mechanical properties for the intended applications.

Experimental Protocol for Measuring the Elution Kinetics

The elastomeric composition containing NaI was cut to the desired length (20 mm), in accordance with the surface/volume ratio (4.80 cm$^{-1}$) desired to be obtained and was immersed in a container of 600 ml of distilled water, thermostated at 20° C.

The container was equipped with a magnetic stirring system driven in a slow rotary motion (100 rev/min) ensuring the homogeneity of the solution. It was covered with a lid in order to reduce water evaportion to a minimum.

1-ml sample were taken daily during the initial period of elution, and weekly after two weeks of elution.

The concentration of iodide or iodate, released daily, was determined by measurement using an iodine-specific electrode:

Two milliliters of solution (K$_2$SO$_4$+ascorbic acid) were added to one milliliter of sample from the container—this solution served as an ion buffer and as a reducing solution in the case where iodates were being measured—together with one milliliter of distilled water. The electrode was immersed in this solution and the electrochemical potential of the solution was measured. A calibration curve established beforehand using iodide solutions containing $5 \times 10^{-5}$ M/l (M: mole) to $5 \times 10^{-2}$ M/l enabled the iodide or iodate concentration (C) to be calculated in mg/l of the solution.

The characteristics of the immersed cylinder were:
Diameter = 10 mm
Height = 20 mm
Surface area = 8.3 cm$^2$
Volume = 1.72 cm$^3$
S/V = 4.80 cm$^{-1}$
Total Weight = 2.04 g
Initial quantity of I(Qo): 0.242 g The results of the elution kinetics are reported in the following table (Table I):

TABLE I

| TIME (DAY) | Cumulative Q (gram) ACTIVE ION | 100 × Q/QO % |
|---|---|---|
| 0.25 | 0.003 | 1.32 |
| 0.92 | 0.007 | 2.62 |
| 1.92 | 0.009 | 3.11 |
| 2.25 | 0.010 | 3.28 |
| 5.00 | 0.011 | 3.75 |
| 12.00 | 0.014 | 4.84 |
| 22.00 | 0.018 | 5.97 |
| 36.00 | 0.027 | 9.06 |
| 50.00 | 0.036 | 12.04 |

Cumulative Q corresponds to the quantity of I equivalent (designated the "active ion") eluted at time t.

With the knowledge that 80% of the active ion incorporated was eluted in accordance with zero-order kinetics with time, the theoretical elution time of the experiment was calculated using the following expression:

$$Te = \frac{0.8 \times Qo}{\text{Daily flow}} \text{ (days)}$$

In the case of Example 1, the theoretical elution time was 333 days.

EXAMPLE 2

The procedure was exactly as in Example 1, except that NaI was replaced with 25 parts of KIO$_3$ with a particle size of from 100 to 200 μm.

A cylinder, the characteristics of which were as follows, was immersed in 600 ml of distilled water, thermostated at 20° C.:
Diameter = 10 mm
Height = 20 mm
Surface area = 8.3 cm$^2$
Volume = 1.72 cm$^3$
S/V = 4.80 cm$^{-1}$
Total weight = 2.04 g
Initial quantity of I (Qo) = 0.169 g The experimental protocol for measuring the elution kinetics was identical with that in Example 1. The results are reported in Table II below:

TABLE II

| TIME (DAY) | Cumulative Q (gram) ACTIVE ION | 100 × Q/QO % |
|---|---|---|
| 0.92 | 0.004 | 2.50 |
| 1.92 | 0.005 | 3.07 |
| 2.25 | 0.005 | 3.16 |
| 5.00 | 0.006 | 3.90 |
| 12.00 | 0.008 | 4.80 |
| 22.00 | 0.010 | 6.20 |
| 36.00 | 0.014 | 8.78 |
| 50.00 | 0.019 | 11.32 |

The theoretical elution time for this example was 353 days.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polycondensation-curable silicone composition for the controlled release of iodine values, comprising (A) at least one diorganopolysiloxane oil bearing at least two condensable or hydrolyzable groups, or a single hydroxyl group, at each end of the polymer chain; (B) a therapeutically effective amount of at least one water soluble, nontoxic, organic and/or inorganic iodine compound which is dispersed homogeneously throughout the composition, in solid or liquid state at ambient temperature and which does not inhibit curing of the composition into an elastomer, molecular iodine being excluded; and (C) a catalytically effective amount of a polycondensation catalyst.

2. The silicone composition as defined by claim 1, further comprising (D) a silane containing at least three condensable or hydrolyzable groups per molecule.

3. The silicone composition as defined by claim 1, comprising from 5 to 130 parts of the iodine compound (B) per 100 parts of the oil (A).

4. The silicone composition as defined by claim 1, wherein the iodine compound (B) comprises an iodide or iodate of the general formulae:

$$(M^{a+})(I^-)_a$$

and $$(M^{a+})(IO_3^-)_a$$

in which a is an integer greater than or equal to 1 and M is an alkali or alkaline earth metal, a transition metal, or a quaternary ammonium $(NY_4)^+$ cation, in which latter the radicals Y, which may be identical or different, are each a linear or branched chain $C_1$-$C_{20}$ alkyl radical or a hydrogen atom.

5. The silicone composition as defined by claim 1, wherein the iodine compound (B) comprises NaI, NaIO$_3$, KI, KIO$_3$, MgI$_2$, M$_g$I$_2$.8H$_2$O, Mg(IO$_3$)$_2$.4H$_2$O, NH$_4$I, FeI$_2$.4H$_2$O or MnI$_2$.

6. The silicone composition as defined by claim 1, said diorganopolysiloxane oil (A) having the general formula (1):

$$Y_nSi_{3-n}O(SiR_2O)_xSiR_{3-n}Y_n \quad (1)$$

in which each R, which may be identical or different, is a monovalent hydrocarbon radical; each Y, which may be identical or different, is a hydrolyzable or condensable group, or a hydroxyl group; n is 1, 2 or 3 with n=1 when Y is a hydroxyl group; and x is an integer greater than 1.

7. The silicone composition as defined by claim 6, the oil of formula (1), x is greater than 10.

8. The silicone composition as defined by claim 6, wherein each radical R is a $C_1$-$C_8$ alkyl, vinyl, phenyl or 3,3,3-trifluoropropyl radical, at least 60% of the number of the radicals R being methyl radicals.

9. The silicone composition as defined by claim 6, wherein each Y is an amino, acylamino, aminoxy, ketiminoxy, iminoxy, enoxy, alkoxy, alkoxyalkyleneoxy, acyloxy or phosphate group.

10. The silicone composition as defined by claim 2, said silane (D) having the formula:

$$R_{4-a}SiY'_a \quad (2)$$

in which R is a monovalent hydrocarbon radical, each Y', which may be identical or different, is a hydrolyzable or condensable group, and a is 3 or 4.

11. The silicone composition as defined by claim 1, in single-component formulation.

12. The silicone composition as defined by claim 1, in two-component formulation.

13. The silicone composition as defined by claim 12, comprising:
(A) 100 parts by weight of an alpha,omega-dihydroxyorganopolysiloxane oil having a viscosity of 50 to 300,000 mPa.s in which the organic radicals are methyl, ethyl, vinyl, phenyl or 3,3,3-trifluoropropyl radicals, at least 60% being methyl radicals, up to 20% being phenyl radicals, and not more than 2% being vinyl radicals;
(B) 10 to 130 parts by weight of the at least one iodine compound;
(C) 0.01 to 1 part by weight of a catalytic tin compound;
(D) 0.5 to 15 parts by weight of a polyalkoxysilane or a polyalkoxysiloxane; and
(E) 0 to 100 parts by weight of a siliceous inorganic filler material.

14. A shaped article comprising the silicone composition as defined by claim 1.

15. The silicone composition as defined by claim 1, in crosslinked elastomeric state.

16. A shaped article comprising the crosslinked elastomeric silicone composition as defined by claim 15.

17. The shaped article as defined by claim 16, controlledly and continuously release about 50 μg of iodine equivalent per liter, to an external aqueous environment.

* * * * *